| United States Patent [19] | [11] Patent Number: 4,609,498 |
|---|---|
| Banasiak et al. | [45] Date of Patent: Sep. 2, 1986 |

[54] PREPARATION OF GOSSYPLURE

[75] Inventors: Dennis S. Banasiak; Edward C. Mozdzen; Jim D. Byers, all of Bartlesville, Okla.

[73] Assignee: Phillips Petroleum Company, Bartlesville, Okla.

[21] Appl. No.: 711,891

[22] Filed: Mar. 14, 1985

[51] Int. Cl.$^4$ ............................................. C11C 3/02
[52] U.S. Cl. ........................... 260/410.9 R; 560/236; 560/247; 260/665 R; 260/665 G; 556/52; 556/187; 568/1; 568/7
[58] Field of Search ............................... 560/236, 247; 260/410.9 R

[56] References Cited

U.S. PATENT DOCUMENTS

| 3,579,602 | 5/1971 | Reusser . |
| 3,778,385 | 12/1973 | Zuech . |
| 3,919,329 | 11/1975 | Anderson et al. . |
| 3,981,940 | 9/1976 | Zuech . |
| 3,987,073 | 10/1976 | Anderson et al. . |
| 3,996,270 | 12/1976 | Friedman et al. . |
| 4,010,217 | 3/1977 | Zuech . |
| 4,247,417 | 1/1981 | Banasiak . |
| 4,248,738 | 2/1981 | Banasiak . |
| 4,269,780 | 5/1981 | Banasiak . |
| 4,296,042 | 10/1981 | Muchowski et al. . |

OTHER PUBLICATIONS

J. Org. Chem. 27, 3395–3400 (1962).
Synthesis, 1977, 817–836.
J. Org. Chem. 39, 3793–3794 (1974).
J.A.C.S. 96, 8115–8116 (1974).
Tetrahedron 33, 1845, 1871–1875 (1977).
Tetrahedron Letters No. 17, 1503–1506 (1979).
The Total Synthesis of Natural Products, vol. 4, 46–50 (John Wiley & Sons, Inc.) (1981).
Liebigs Ann. Chem. 1982, 1478–1494.
J. Organometal. Chem. 250, 1–12 (1983).

*Primary Examiner*—Helen M. S. Sneed
*Attorney, Agent, or Firm*—Stephen E. Reiter

[57] ABSTRACT

Process for the production of the insect sex attractant, gossyplure, is provided. The process comprises first disproportionating 1,5-cyclooctadiene and 1-hexene to give 1,5,9-tetradecatriene, then metallating the triene to form a 1-metallo-5,9-tetradecadiene, and finally treating the organometal compound with a $C_2$-synthon to give directly 7,11-hexadecadienyl acetate or a substituted 7,11-hexadecadienyl moiety which can readily be converted to the desired acetate.

19 Claims, No Drawings

PREPARATION OF GOSSYPLURE

BACKGROUND

This invention relates to the preparation of gossyplure.

Gossyplure, a mixture of 7,11-hexadecadienyl acetate stereoisomers, is a known pheromone for several insect species. In order to make this compound widely available for use in insect control, economic large scale synthetic conversion processes must be developed. While synthetic routes for the preparation of gossyplure have been disclosed in the prior art, the known routes suffer from the disadvantages of requiring multiple reaction steps with consequent low over all product yield, consumption of large quantities of reagents which do not contribute to the final product structure and the like.

For example, in U.S. Pat. No. 3,919,329 (1975), Anderson and Henrick disclose a multistep synthesis which involves (1) the oxidation of 1,5-cyclooctadiene to 1,2-epoxy-5-cyclooctene, (2) oxidation of the epoxide to 2-hydroxy-5-cycloocten-1-one, (3) oxidative cleavage of the α-hydroxyketone to an alkyl-8-oxo-4octenoate, (4) Wittig reaction of the octenoate to yield (4Z, 8Z/E)-4,8-tridecadienoate, (5) reduction of the dienoate to a dienol, (6) conversion of the dienol to the mesylate, which is then (7) converted to the iodide or bromide, which is finally (8) coupled with a cuprate reagent prepared from cuprous iodide and the lithium reagent obtained from the reaction of lithium and the bromo-acetal obtained from 3-bromo-1-propanol and ethyl vinyl ether. The product acetal is (9) hydrolyzed to 7,11-hexadecadienol, and finally (10) converted into the acetate using acetic anhydride in pyridine.

In U.S. Pat. No. 3,996,270 (1976), Friedman and Chanan describe an alternative multistep synthesis of gossyplure which involves (1) butylation of the monoanion of 1,5-hexadiyne, (2) partial reduction of the resulting 1,5-decadiyne in sodium/liquid ammonia to yield deca-(E)-5-enyne, (3) alkylation of the enyne with hexamethylene halohydrin or a protected derivative thereof, (4) acetylation of the product of step (3), which product is then (5) partially reduced in the presence of hydrogen and Lindlar catalyst. This synthesis requires several starting chemicals which are not readily available on large scale, e.g. 1,5-hexadiyne and hexamethylene halohydrin, and depend for the desired product stereochemistry on two separate hydrogenation steps.

Yet another multistep synthetic route for the preparation of gossyplure has been proposed by Muchowski and Venuti, as disclosed in U.S. Pat. No. 4,296,042 (1981). Thus (1) an omega-hydroxyalkyl diphenyl phosphine is converted into a cyclic polymethylene 1,1-diphenyl phosphonium bromide, (2) the cyclic phosphonium bromide is then converted into a cyclic phosphonium ylid by treatment with an alkali metal alkoxide, then (3) coupled with a protected aldehyde or ketone to produce a phosphine oxide. The phosphine oxide is (4) treated with an organolithium compound, then (5) coupled with a second aldehyde and finally (6) the resulting lithium salt is decomposed, producing a crude, protected dien-ol. The protected dien-ol is (7) hydrolyzed and esterified by treatment with acetic acid/acetyl chloride. Again, numerous reaction steps are required as the desired chain length and stereochemistry are achieved in a piecemeal fashion.

In summary, due to the large number of reaction steps required, the relative inavailability of many needed reagents and the step-wise fashion in which the desired carbon backbone is constructed, known synthetic routes for the production of gossyplure are not amenable to being carried out economically on a large scale.

OBJECTS OF THE INVENTION

An object of the invention, is an efficient and economic process for the synthesis of gossyplure.

This and other objects will become apparent fron further study of the disclosure and claims herein provided.

STATEMENT OF THE INVENTION

In accordance with the present invention, we have discovered that disproportionation of 1,5-cyclooctadiene and 1-hexene in the presence of a disproportionation catalyst produces 1,5,9-tetradecatriene having a high selectivity to cis double bond at C-5 and greater than a thermodynamic ratio of cis/trans double bond at C-9, i.e., the desired stereochemistry at both double bonds for ultimate use as an insect sex attractant. Metallation of the resulting 1,5,9-tetradecatriene produces 1-metallo-5,9-tetradecadiene which can then be reacted with a $C_2$-synthon to give gossyplure directly or a functionally substituted $C_{16}$ compound which can conveniently be converted to gossyplure.

DETAILED DESCRIPTION OF THE INVENTION

In accordance with the present invention, a process for the preparation of gossyplure is provided comprising:

(a) disproportionating 1,5-cyclooctadiene and 1-hexene in the presence of a disproportionation catalyst under disproportionation conditions suitable to give 1,5,9-tetradecatriene, (b) metallating the resulting 1,5,9-tetradecatriene with a metallating agent under suitable conditions to give a 1-metallo-5,9-tetradecadiene, (c) contacting the 1-metallo-5,9-tetradecadiene obtained from step (b) with a $C_2$-synthon which is reactive with the metallo-substituted diene to give gossyplure directly or a 1-substituted-7,11hexadecadiene wherein the 1-substituent can readily be converted to the acetate, thereby giving gossyplure.

The disproportionation of 1,5-cyclooctadiene and 1-hexene can be carried out in a variety of ways as recognized by those of skill in the art. Thus, any suitable ratio of 1,5-cyclooctadiene/1-hexene can be employed in the presence of a wide variety of disproportionation catalysts. For most efficient utilization of the olefinic reactants, a molar ratio of about 1:1 is preferred, although good converions are obtained with 1,5-cyclooctadiene/1-hexene ratios ranging from about 5:1 to about 1:5.

A wide variety of heterogeneous and homogeneous disproportionation catalysts are known in the art and are capable of promoting the disproportionation of 1,5-cyclooctadiene plus 1-hexene to produce 1,5,9-tetradecatriene. Our invention is not limited to the use of a specific disproportionation catalyst, but any catalyst suitable for disproportionation of 1,5-cyclooctadiene and 1-hexene can be utilized.

Suitable heterogeneous catalysts useful in the practice of the present invention include:

(1) silica or thoria promoted by an oxide or compound convertible to an oxide by calcination, or sulfide of tungsten or molybdenum; or by an oxide or compound convertible to an oxide by calcination of rhenium or tellurium;

(2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

(3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;

(4) silica, alumina, aluminum phosphate, zirconium phosphate, calcium phosphate, magnesium phosphate, or titanium phosphate promoted by a hexacarbonyl of molybdenum or tungsten; and (5) (a) molybdenum oxide or tungsten oxide associated with suitable support material and (b) at least one organoaluminum compound, optionally, treated with nitric oxide or nitrosyl halides.

The catalysts of (1) can be prepared and activated by conventional techniques such as by combining a catalyst grade silica with suitable tungsten, molybdenum, rhenium or tellurium compounds by a conventional method such as, for example, impregnation, dry mixing, or co-precipitation. Suitable tungsten and molybdenum compounds include tungsten oxide and molybdenum oxide and compounds convertible to these oxides. The supported oxides are activated by calcining in air and the support sulfides are activated by heating in an inert atmosphere.

The catalysts of (2) can be prepared and activated by conventional techniques such as by combining catalyst grade alumina with an oxide or a compound convertible to an oxide by calcination of molybdenum, tungsten or rhenium and calcining the resulting mixture after removal of any solvent used in the impregnation. The sulfides of tungsten or molybdenum or the salts of phosphomolybdic acid can be utilized to impregnate a catalyst grade alumina by solution in a proper solvent after which the solvent is evaporated and the resulting mixture dried to prepare the catalyst.

The catalyst composition of (3) can be prepared and activated by conventional techniques. For example, molybdenum oxide can be co-precipitated with aluminum phosphate followed by calcination in air to produce an activated catalyst. Alternatively, the support material can be impregnated with a compound of the promoter convertible to the oxide, such as ammonium tungstate, followed by calcination in air. In the preparation of a sulfide-containing catalyst, a sulfide of the promoter can be ball-milled with a support, such as zirconium phosphate, followed by heating in an inert atmosphere such as nitrogen. Magnesium tungstate and beryllium phosphotungstate can be dry mixed with titanium phosphate, for example, and activated by calcination in air at elevated temperatures.

The catalyst compositions of (4) can be prepared and activated by impregnating a previously calcined support material sach as calcium phosphate with a solution of the hexacarbonyl of the promoter in an organic solvent such as benzene, followed by drying in a vacuum or in an inert atmosphere at about 50° to 700° F.

The (a) components of the catalyst system (5) are active by themselves for the disproportionation of olefins. However, the activity of this system is exhibited at relatively high temperatures which are generally above 150° C. for optimum operation.

Suitable support materials which are combined with the oxides of molybdenum and tungsten to form the (a) component of the catalyst system (5) include alumina, silica, silica-alumina magnesia-titania, thoria, aluminum phosphate, zirconium phosphate, titanium phosphate, calcium phosphate, magnesium phosphate, and mixtures thereof.

Preferred combinations of the above support materials with the oxides of molybdenum and tungsten promoter materials include (i) silica or thoria promoted by the oxide or a compound convertible to an oxide by calcination of tungsten or molybdenum; (ii) alumina promoted by an oxide, or compound convertible to an oxide by calcination of molybdenum or tungsten; and (iii) one or more of the group aluminum phosphate, zirconium phosphate, calcium phosphate, magnesium phosphate, or titanium phosphate promoted by one or more of an oxide of molybdenum or tungsten, or by a compound of molybdenum or tungsten convertible to an oxide by calcination.

The combinations of (i), (ii), or (iii) can be prepared and activated by suitable methods such as, for example, impregnation, dry mixing, or co-precipitation.

When the promoter is tungsten oxide, the preferred support material is silica or silica-containing materials. The preferred support material for molybdenum oxide is alumina or alumina-containing materials. In general the (a) component of the catalyst system (5) will contain about 0.1 to about 30, preferably from about 1 to about 15 weight percent of the molybdenum or tungsten oxide. In addition, it is sometimes desirable that this component of the catalyst system of the invention contain relatively small amounts, from about 0.005 to about 5, preferably 0.1 to 2, weight percent of an inorganic base material. Suitable inorganic base materials include alkali metal and alkaline earth metal hydroxides and carbonates, sodium hydroxide, potassium hydroxide, sodium carbonate and potassium carbonate being preferred.

The solid (a) component of the system (5) catalysts can be in any conventional catalytic shape or size, depending upon the type of conversion in which it is to be utilized. For example, in fixed bed catalyst systems, the solid composite can be in the form of spheres, pellets, extrudates, agglomerates and the like. In slurry catalyst systems, the solid can be in the form of relatively small particles or in the form of a power.

To be effective in the present catalyst system, the above-described (a) component of the catalyst system (5) is activated at elevated temperatures, generally in flowing air. The activation of the catalysts is accomplished at a temperature ranging from about 500° to 1600° F. for a period of several seconds to several hours. When the (a) component of the catalyst system is tungsten oxide on silica, a convenient and economical activation treatment is in the temperature range of about 900° to 1200° F. for a period of 15 minutes to 5 hours. When the (a) component of the catalyst system (5) is molybdenum oxide on alumina, a convenient and economical treatment is in the temperature range of about 900°–1400° F. for 0.5 to 20 hours or longer. In some cases the activation using an oxygen-containing gas can be followed by treatment, also at elevated temperatures, with other treating gases such as carbon monoxides, hydrogen and the like.

The organoaluminum compounds which are applicable for use as the (b) component in catalyst (5) have the formula $R''_aAlX_b$ where $R''$ is a saturated aliphatic or aromatic hydrocarbon having up to about 20 carbon atoms. X is chlorine, bromine, iodine, or fluorine, a is an integer of at least 1, b can be 0, 1 or 2, and the total of a and b is 3, thus a can be 1, 2 or 3. Such aluminum compounds are well known in the art and are generally commercially available.

Some examples of suitable organoaluminum compounds halide are methylaluminum dichloride, dimethylaluminum fluoride, methylaluminum sesquichloride, trimethylaluminum, ethylaluminum dichloride, ethylaluminum sesquichloride, di-(2-ethylhexyl)aluminum bromide, triisobutylaluminum, phenylaluminum dichloride, di(3-methylpentyl)aluminum bromide, cyclohexylaluminum dichloride, benzylaluminum diodide, dieicosylaluminum bromide, and the like, and mixtures thereof. The preferred (b) components are the organoaluminum halides, especially those wherein the hydrocarbon portion is an alkyl radical of 1 to 5 carbon atoms. Particularly good results are obtained with ethylaluminum dichloride, diethylaluminum chloride, and mixtures such as ethylaluminum sesquichloride and methylaluminum sesquichloride.

The molar proportion of the organoaluminum (b) component to the solid (a) component to form the catalyst system (5) useful in the practice of the present invention will generally be in the range of from about 0.005:1 to 20:1, preferably from about 0.01:1 to 10.:1 moles of the (b) component per mole of the molybdenum or tungsten oxide contained in the (a) component.

It is sometimes preferred that the supported tungsten or molybdenum component, before contacting the organoaluminum compound, be treated either with nitric oxide or with a nitrosyl halide. Such treatment can take place at a temperature preferably in the range of about 0° to 130° C., more preferably about 20° to 60° C., for a time in the range of from a few seconds up to about 24 hours, and preferably in the presence of a diluent in which the nitric oxide or nitrosyl halide is at least partially soluble. After such treatment, the diluent and excess nitric oxide or nitrosyl halide can be removed from the solid catalyst by decantation, evaporation, and similar techniques. This treatment, however, should be carried out in the substantial absence of moisture, preferably in an inert atmosphere, to prevent the effects of the previous activation by calcination.

The catalyst system (5) useful in the practice of the present invention is prepared simply by combining the solid (a) component with the organoaluminum (b) component under conditions of time and temperature which permit the catalytically active catalyst composition to be formed. The combination occurs very readily, and, in general, the components can be mixed at any convenient temperature, room temperature frequently being satisfactory, in the presence of a diluent in which the organoaluminum compound is at least partially soluble. Any convenient diluent such as, for example, benzene, cyclohexane, toluene, chlorobenzene, methylene chloride, ethylene chloride, and the like, can be used for this purpose. Halogenated diluents are generally preferred. The mixing of these two catalyst components is carried out in the substantial absence of air or moisture, generally in an inert atmosphere. After the catalytic reaction mixture is formed, it need not be isolated but can be added directly to the olefin reaction zone as a suspension in its preparation medium. If desired, the catalyst components can be separately added, in any order, to the reaction zone either in the presence or absence of the feed olefin.

Alternatively, the system (5) catalysts useful in the practice of the invention can be separated from the preparation medium and the dissolved organoaluminum compound therein by decantation, and, after additional washing and/or drying if desired, can be added to the reaction zone as a solid rather than as a suspension.

The operating temperature for the process of this invention when using heterogeneous catalysts of (1) is in the range of about 400° to 1100° F. The process of this invention when using the catalysts of (2) will be operated at a temperature in the range of about 150° to 500° F. The process using the catalysts of (3) will be carried out in a temperature range of about 600° to 1200° F. The process using the catalysts of (4) will be carried out in a temperature range of about 0° to 600° F. In the process of the invention, pressures are not important but will be generally in the range of about 0 to 2,000 psig.

According to the process of the invention employing catalyst system (5) the mixture of olefins to be converted, i.e., 1,5-cyclooctadiene and 1-hexene, is contacted with the catalyst under conditions suitable to obtain the desired reaction, for example, at a temperature in the range of about 0° to 150° C. and at any convenient pressure. Preferably, the temperature is in the range of about 15° C. to 50° C. wherein good results are obtained economically. Excellent results are obtained by contacting the olefin feed material with the catalyst at room temperature. The conversion can be carried out in the presence of any inert diluent such as that used for the catalyst preparation, if desired. Diluents are not essential but are sometimes preferred and such diluents can include saturated aliphatics and aromatics such as cyclohexane, xylene, isooctane, and the like, and halogenated derivatives thereof. The time of contact will depend upon the desired degree of conversion and the catalysts utilized, but will, generally, be in the range of from 0.1 minute to 24 hours, preferably 5–120 minutes. The proportion of catalyst composition to olefin feed in the reaction zone will generally be in the range of from about 0.001 to 100 millimoles of the molybdenum or tungsten oxide contained in the solid catalyst, for each mole of olefin in the reacting zone.

The oxide-promoted catalysts useful in the practice of this invention are activated by heat treatment at temperatures of from 600° to 1500° F. for a period of about 1 second to 25 hours or more, shorter times being used with higher temperatures and longer times with the lower temperatures. A convenient and economical treatment is obtained by subjecting the catalyst to contact with a stream of air at a temperature in the range of about 900° to 1200° F. for from about 15 minutes to 5 hours. Other gases, which do not poison the catalyst, for example, nitrogen, can also be sometimes used either as a substitute for the air treatment, or as a subsequent flush. Air is usually preferred for activation, since it is readily available.

Any conventional contacting technique can be used for the olefin disproportionation employing the heterogeneous catalysts disclosed herein, and batchwise or continuous operation can be utilized. After the reaction period, the products can be separated and/or isolated by any suitable means such as by fractionation, crystallization, adsorption, and the like. Unconverted feed materials or products not in the desired molecular weight range can be recycled to the conversion zone. After separation of the products, the solid catalyst can be recycled to the reaction zone either with or without the addition of a fortifying amount of organoaluminum halide.

The heterogeneous catalysts employed in the practice of the invention can be further treated with modifying amounts of compounds of alkali metals or alkaline earth metals.

The catalyst supports and promoting agents employed can contain other materials which do not have a deleterious effect on the desired reaction or promote the formation of undesired by-products.

Suitable homogeneous catalysts employed in the practice of the present invention include:

(a) the coordination compounds of molybdenum or tungsten or disclosed in U.S. Pat. No. 3,778,385, which disclosure is hereby incorporated by reference;

(b) the coordination compounds of molybdenum or tungsten complexed with NO, together with an organoaluminum adjuvant, as disclosed in U.S. Pat. No. 4,010,217, which disclosure is hereby incorporated by reference;

(c) the neutral carbene complex catalysts disclosed in U.S. Pat. No. 4,247,417, which disclosure is hereby incorporated by reference;

(d) the neutral carbene complex catalysts disclosed in U.S. Pat. No. 4,248,738, which disclosure is hereby incorporated by reference;

(e) the neutral carbene complex catalysts disclosed in U.S. Pat. No. 4,269,780, which disclosure is hereby incorporated by reference;

(f) other homogeneous catalysts known by those of skill in the art such as, for example, $WCl_6 + SnMe_4$; $W(CH_2C_6H_5)_3Cl + AlCl_3$; $WOCl_4 + R_4Sn$; and the like.

It is also recognized by those of skill in the art that the homogeneous catalysts detailed herein can be deposited on solid support and employed as solid phase catalysts.

The metallation of 1,5,9-tetradecatriene to form 1-metallo-5,9-tetradecadiene can be carried out employing a variety of metallating agents. Any metallating agent capable of selective reaction with the terminal double bond of the triene starting material is suitable. Examples of suitable metallating agents include organoboranes, organoaluminum compounds, organomagnesium compounds, organozirconium compounds and the like.

Organoboranes contemplated to be within the scope of the present invention can be described as "hindered" organoborane compounds and can be represented by the following formula:

$$R_2BH$$

wherein each R is independently a $C_1$ to $C_{10}$ carbon radical wherein at least one R group is a secondary or tertiary alkyl group and each R group can be connected to the other as part of a ring structure. Exemplary compounds which satisfy the above formula include disiamylborane (i.e., bis-(3-methyl-2-butyl)borane), 9-borabicyclo[3.3.1]nonane (9-BBN), dithexylborane, thexylcyclopentylborane, thexylcyclohexylborane, and the like.

The hydroboration reaction is generally carried out in the presence of a suitable solvent such as, for example, tetrahydrofuran (THF). A roughly equimolar mixture of triene and organoborane reagent are combined. Preferably, a slight excess of triene is employed to minimize the likelihood of hydroboration occurring on the internal double bonds of the starting material triene. Typically, the hydroboration reaction should be carried out in an inert atmosphere; i.e. moisture and oxygen should be excluded from the reaction mixture. Reaction conditions employed are broadly 0°–100° C. for a few minutes up to several hours. Preferably, the hydroboration is carried out at about 20°–80° C. for 15 minutes up to about 2 hours. Reaction is generally carried out at about atmospheric pressure, although higher and lower pressures are acceptable.

Once the reaction of the triene and organoboron compound is complete, the resulting 1-metallo-5,9-tetradecadiene is ready for further reaction with an appropriate $C_2$-synthon as detailed more fully below.

Organoaluminum compounds contemplated to be within the scope of the present invention can be described by reference to the formula:

$$R_2AlH$$

wherein R is as defined above. Examples of suitable organoaluminum compounds include diisobutylaluminum hydride, diisopropylaluminum hydride and the like.

Organozirconium compounds contemplated to be within the scope of the present invention can be described by the formula:

$$(Ar)_2Zr(X)H$$

wherein Ar is an aromatic ligand having 5–10 carbon atoms, such as phenyl, cyclopentadienyl, methylcyclopentadienyl, and the like, and X is a halogen. Examples of suitable organozirconium compounds include biscyclopentadienylzirconium chlorohydride, biscyclopentadienyl bromohydride, bispentamethylcyclopentadienyl chlorohydride, bismethylcyclopentadienyl chlorohydride, bisdimethylcyclopentadienyl chlorohydride, and the like.

Organomagnesium compounds contemplated to be within the scope of the present invention can be described by reference to the following formulae:

$$R'MgX, \text{ and}$$

$$R'_2Mg$$

wherein R' has at least one β-hydrogen, and therefore is a $C_2$ to $C_{10}$ carbon radical and X is Cl, Br or I. Exemplary compounds which satisfy the above formulae include various Grignard reagents, such as, for example, ethylmagnesium bromide, isopropylmagnesium bromide, butylmagnesium bromide, and the like. Additional examples include dialkylmagnesium compounds such as, for example, diethylmagnesium, diisopropylmagnesium and the like.

Metallation with organomagnesium compounds is generally carried out in the presence of at least one transition metal activating agent. Suitable transition metal activating agents include nickel, titanium, vanadium and zirconium compounds. Exemplary titanium activating agents include a titanocene dichloride such as, for example, dicyclopentadiene titanium dichloride, or alternatively, titanium tetrachloride. The molar ratio of organomagnesium compound to triene should be at least about 1:1 with the presence of a small excess of the organomagnesium compound acceptable, i.e., up to about to a 1.5 to 1 molar ratio. The molar ratio of triene to transition metal reagent is generally in the range of about 1-500:1 and preferably about 50-100:1.

Metallation with organomagnesium compounds is generally carried out at atmospheric pressure, although higher and lower pressures are operable. Preferably, atmospheric pressure or slightly reduced pressures will be employed since pressures in excess of atmospheric will tend to retard the reaction rate. Reaction temperatures of about 31 20° to about 100° C. for at least one minute up to about 24 hours are suitable. Preferably, reaction temperature will be maintained between about 0° and 60° C., for about 15 minutes to about 6 hours.

Conversion of the 1-metallo-5,9-tetradecadiene to a 1-substituted-7,11-hexadecadiene can be carried out by contacting the metallo-diene with a variety of $C_2$-synthons which are reactive with the organometallic species. Exemplary reactive $C_2$-synthons include ethylene oxide, bromoethyl acetate ($BrCH_2CH_2OCOCH_3$), ethyl bromoacetate ($BrCH_2CO_2Et$), diethyl bromomalonate, chloroethyl acetate, ethyl chloroacetate, iodoethyl acetate, ethyl iodoacetate and the like. The product is a substituted hexadecadiene or derivative thereof, which has the empirical formula, $C_{15}H_{27}Z$, wherein Z is selected from the group consisting of $—CH_2OH$, $—CO_2CH_3$, and $—CH_2OCOCH_3$.

The 1-metallo-5,9-tetradecadiene can be contacted with an appropriate $C_2$-synthon under suitable reaction conditions to cause the formation of a new carbon-carbon sigma bond. Thus, for example, an organoborane can be contacted with a halo-ester in the presence of a suitable base such as, for example, potassium t-butoxide. Alternatively, an organomagnesium compound can be contacted with ethylene oxide or a halo-ester, optionally in the presence of a copper (I) salt. Typical reaction conditions comprise inert atmosphere at −20° to 80° C. for 0.5 to 10 hours. Preferably, reaction is carried out at about −10° to +20° C. for 1-2 hours.

When a copper (I) salt is employed to promote the reaction of the 1-metallo-5,9-tetradecadiene and the $C_2$-synthon, only catalytic amounts are required. Thus, about 1-20 mole % copper (I) salt based on the moles of organometallic species employed are suitable. Preferably, about 2-10 mole % copper (I) salt will be used. Suitable copper (I) salts include copper (I) iodide, copper (I) bromide, copper (I) chloride and the like.

Where Z above is methoxy ($—CH_2OH$), the product need only be esterified employing techniques well known to those of skill in the art in order to convert the hydroxy substituted hexadecadiene into gossyplure. Where Z above is acetoxy ($—CO_2CH_3$), the carbonyl function can conveniently be reduced to the alcohol by techniques known to those of skill in the art, such as, for example, reduction with lithium aluminum hydride, to give an alcohol which can then be converted to gossyplure by standard esterification techniques Where Z is $—CH_2OCOCH_3$, i.e., when the $C_2$-synthon employed is bromoethyl acetate, chloroethyl acetate or iodoethyl acetate, gossyplure is obtained directly as the product of the conversion of the 1-metallo-5,9-tetradecadiene.

A further understanding of the present invention and its advantages will be provided by reference to the following examples.

EXAMPLE I

Preparation of 1,5,9-Tetradecatriene a. Homogeneous catalyst

Equimolar quantities of 1,5-cyclooctadiene and 1-hexene were mixed in an inert atmosphere in an autoclave. The catalyst charge of about 0.0025 mole of (phenylmethoxycarbene)pentacarbonyltungsten(O) per mole of cyclooctadiene was added as a 0.1 molar solution in chlorobenzene along with approximately 0.025 mole of carbon tetrachloride as a catalyst modifier. A small amount of hexadecane (0.05-0.10 mole) was added in a precisely weighed amount as an internal standard for subsequent analysis by gas liquid chromatography (GLC).

The reaction was started and the reaction mixture was held at reaction temperature for about 2 hours after which time it was cooled, removed from the reactor and analyzed. Table I shows the results obtained from operating in the temperature range 84°-92° C.

TABLE I

Preparation of 1,5,9-Tetradecatriene from 1,5-cyclooctadiene and 1-Hexene Using Homogenous (Phenylmethoxycarbene)-pentacarbonyl tungsten (O) Catalyst

| Run No. | Temp °C. | Press. psi | $COD^a$ Conv., % | $TDT^b$ Yield, % | Selectivity to TDT, % |
|---|---|---|---|---|---|
| 1 | 92 | 120-140 | 50 | 16 | 31 |
| 2 | 86 | 114-130 | 57 | 15 | 27 |
| 3 | 84 | 118-130 | 57 | 15 | 26 |

Time = 2 hrs
$^a$COD = 1,5-Cyclooctadiene
$^b$TDT = 1,5,9-Tetradecatriene
(Phenylmethoxycarbene)pentacarbonyltungsten (O) was prepared by known literature procedures (e.g. Cardin, D. J. et al. Chem. Rev. 72 545 (1972))

b. Heterogeneous Catalyst

An alumina-supported cobalt molybdate catalyst (American Cyanamide HDS-20A; 78.7 wt.% $Al_2O_3$) was activated by heating in air at 350° C. for 3 hours, then under argon for about 0.5 hours, as the catalyst bed was cooled to about 130°-160° C. for reaction. A 1:1.2 molar ratio of 1,5-cyclooctadiene:1-hexane was prepared over the above described activated catalyst at 130°-160° C. and 4-10 weight hourly space velocity (WHSV). GLC analysis indicated about 16% conversion of cyclooctadiene feed and about 38% selectivity (or about 6% yield) to 1,5,9-tetradecatriene.

EXAMPLE II

Coupling of 1,5,9-Tetradecatriene with Ethyl Bromoacetate using 9-Borabicyclononae 1,5,9-Tetradecatriene (20 grams, 0.104 mole) in 50 mL of tetrahydrofuran was placed in a thoroughly dried 1 liter flask equipped with dropping bottle and a magnetic stirrer. An atmosphere of nitrogen was maintained in the flask. A tetrahydrofuran solution of 9-borabicyclononane (9-BBN) (200 mL of a solution containing 0.100 mole of 9-BBN) was added slowly over about 15 minutes and the temperature was raised to reflux for 1 hour. The mixture was cooled to near 0° C. and 50 mL of tertiary butyl alcohol and 17 grams of ethyl bromoacetate was added. One hundred milliliters of a 1 molar solution of potassium tertiary-butoxide and tertiary butyl alcohol was added dropwise over 0.5 hour. The cloudy aqueous solution was warmed to room temperature and 33 mL of 3 molar aqueous sodium acetate solution was added followed by 22 mL of 30% hydrogen peroxide which was added dropwise. After stirring for an additional 30 minutes at room temperature the mixture was diluted with saturated aqueous sodium chloride and the solution was extracted with an approximately equal volume of diethyl ether. The separated ether solution was washed once with an approximately equal volume of saturated aqueous sodium chloride and dried over anhydrous magnesium sulfate. After filteration to remove the magnesium sulfate and simple distillation to remove the volatiles the yield was determined by GLC using a precisely weighed amount of methyl undecenoate as a standard. The results of several runs are shown in Table II.

TABLE II

Coupling of 1,5,9-Tetradecatriene (TDT) with Ethyl Bromoacetate Using 9-Borabicyclononane (BBN)

| Run No. | Solvent | Run After BBN Addition Hrs. | Run After BBN Addition Temp. °C. | TDT Conv. % | EHDD[a] Yield % | EHDD[a] Select. % |
|---|---|---|---|---|---|---|
| 4 | THF[b] | 1 | reflux | 64 | 36 | 56 |
| 5 | THF | 1 | 50 | 52 | 44 | 84 |
| 6 | C6[c] | 3 | reflux | 92 | 28 | 30 |
| 7 | C6 | 1 | 50–65 | 61 | 47 | 78 |
| 8 | C6 | 1 | room temp. | 68 | 27 | 41 |
| 9 | C6/THF | 1.5 | 50 | 44 | 17 | 38 |
| 10 | THF | 1 | room temp. | 40 | 8 | 21 |
| 11 | C6 | 5.5 | room temp. | 51 | 49 | 95 |
| 12 | C6 | 1 | room temp. | 50 | 45 | 90 |
| 13 | C6 | 1 | 50 | 48 | 44 | 91 |
| 14 | THF | 1 | room temp. | 48 | 39 | 81 |
| 15 | THF | 1 | reflux | 56 | 35 | 63 |
| 16 | C6 | 5 | reflux | 61 | 44 | 72 |

[a]EHDD = Ethyl Hexadecadienoate
[b]THF = Tetrahydrofuran
[c]C6 = n-Hexane

It is seen that lower reaction temperatures favor higher selectivities and that longer reaction times favor higher conversions. The reasons for the inconsistencies shown such as in the extreme example in no. 10, are not known, but it is suspected that may be due to inconsistencies in excluding moisture from the potassium tertiary-butoxide solutions.

EXAMPLE III

Reduction of Ethylhexadecadienoate to 7,11-Hexadecadien-1-ol

The ethylhexadecadienoate was reduced with lithium aluminum hydride (LAH) in tetrahydrofuran as follows. An oven dried 3-neck flask equipped with a magnetic stirrer, reflux condenser and an additional funnel was charged with 2 equivalents of LAH in dry tetrahydrofuran (THF). The reaction vessel and contents were maintained under a positive flow of nitrogen as 1 equivalent of ester (ethylhexadecadienoate) dissolved in an equal volume of dry THF was added dropwise to the stirred LAH suspension at a rate to maintain the THF at a gentle boil. After ester addition was complete, the reaction mixture was refluxed gently for an additional 2 hours, cooled to 0° C. and one equivalent of water slowly added to decompose excess LAH, followed by addition of 15% aqueous NaOH. The resulting gray gel was filtered and the organic layer washed with water, dried over adsorbent and concentrated on a rotary evaporator. Yields of about 41% of the desired 7,11-hexadecadien-1-ol were obtained.

The product alcohol was esterified without further purification.

EXAMPLE IV

Acetylation of 7(Z),11(Z,E)-Hexadecadien-1-ol

Twenty-eight grams of 7,11-hexadecadien-1-ol and 50 mL of acetic acid were reacted in 100 mL of refluxing toluene for 8 hours. The mixture was cooled, washed twice wwith water, once with a saturated sodium chloride solution and then dried over magnesium sulfate. The mixture was filtered, reduced in volume using a rotary evaporator and then distilled at reduced pressure through a short Vigreaux column. The gossyplure fraction boiling at 111°–114° C. at 0.05 millimeters of mercury was collected and analyzed.

A crude yield of 54% of the gossyplure was obtained. Analysis showed that the double bond in the 11-position was about 62% trans (E) and 38% in (Z).

EXAMPLE V

Coupling of 1,5,9-tetradectriene with ethylene oxide using Butylmagnesium Chloride 1,5,9-Tetradecatriene (10 g, 0.052 mol; 88% purity by GLC), butylmagnesium chloride (18 mL of 2.8M in diethyl ether; 0.05 mol) and titanocene dichloride [bis(cyclopentadienyl)titanium dichloride; 0.15 g, 0.6 mmol] were stirred under an inert atmosphere at room temperature. After about three hours, the reaction mixture was cooled to about 0° C. and cuprous bromide (0.035 g, 0.2 mmol) and tetrahydrofuran (THF; 20 mL) were added. The reaction mixture was maintained between about 0°–15° C. while ethylene oxide (EO; 3.2 mL, 0.063 mol) was added slowly. Once EO addition was complete, the reaction mixture was stirred for an additional hour at 0° C. Acetyl chloride (7.4 mL, 8.17 g, 0.1 mol) was then added dropwise to the reaction mixture. The reaction temperature rose to about 45° C. by the time acetyl chloride addition was complete. The rection mixture was stirred overnight at room temperature before workup for GLC analysis.

Workup involved pouring the reaction mixture into an equal volume of cold water, separating and washing the organic layer with saturated sodium bicarbonate solution, drying the organic layer over MgSO4, filtering and removing the solvent on a rotary evaporator. GLC analysis indicated a 37% yield of gossyplure, based on triene starting material.

EXAMPLE VI

Ten grams of 1,5(E),9(E,Z)-tetradecatriene (52 mmole), 31.2 mL of 2 molar butylmagnesium chloride (62.4 mmole) in diethyl ether and 0.65 g of titanocene dichloride (2.6 mmole) were mixed under an inert atmosphere and stirred at room temperature for two hours. The mixture was cooled to −30° C. and 50 mL of tetrahydrofuran was added. Cuprous bromide (2.24 g, 7.8 mmole) was added followed by ethylene oxide (63.2 mmole) which was added slowly with cooling to maintain the temperature of the reaction mixture in the range of −30° to 0° C. Vigorous stirring was continued for about an hour while the temperature was held below 5° C.

The product mixture was mixed first with ethyl acetate and washed with 4.5 molar HCl (about 2.5 moles HCl per mole of the starting triene), separated and then washed with a saturated aqueous sodium bicarbonate solution to remove any residual acid left in the organic layer. The yield of 7(Z)1,11(E,Z)-hexadecadien-1-ol as determined by GLC was 44%.

The 7(Z),11(Z,E)-hexadecadien-1-ol can readily be separated by distillation. Most of the yields shown in the following tabulations were determined by GLC using a methyl silicone coated capillary column held at 80° C. for 2 minutes followed by temperature programmed increase of 10° C./minute up to 250° C.

TABLE III

Preparation of 7(Z),11(Z,E)-Hexadecadien-1-ol from 1,5,9-Tetradecatriene Using Grignard Exchange in Presence of Titanocene Dichloride Followed by Ethylene Oxide Addition in Presence of CuBr

| Run | Grignard Reagent RMgCl R | RMgCl mmoles | Cp$_2$TiCl$_2$[a] mmoles | 1,5,9-Tetra-decatriene mmoles | Ethylene Oxide (EO) Reaction mmoles | Solvent type[b] | ml | temp. °C. | CuBr mmole | Yield[c] % |
|---|---|---|---|---|---|---|---|---|---|---|
| 1 | n-butyl | 62.4 | 2.6 | 52 | 63.2 | THF | 50 | <0–30 | 3.9 | 35 |
| 2 | " | 62.4 | 2.6 | 52 | 63.2 | THF | 50 | −5–28 | 2 | 37 |
| 3 | " | 62.4 | 1.6 | 52 | 63.2 | THF | 50 | −5–33 | 1 | 39 |
| 4 | " | 62.4 | 1.6 | 52 | 63.2 | THF | 50 | −5–38 | 0.5 | 41 |
| 5 | " | 62.4 | 1.6 | 52 | 63.2 | THF | 50 | −5–37 | 0.24 | 40 |
| 6 | " | 62.4 | 1.6 | 52 | 63.2 | THF | 50 | −5–0 | 0 | 1 |
| 7 | " | 1248. | 48.2 | 1039.8 | 1263.1 | THF | 1000 | −5–15 | 9.8 | 46* |
| 8 | " | 62.4 | 1.0 | 52 | 63.2 | THF | 50 | −5–42 | 0.49 | 42 |
| 9 | " | 62.4 | 1.6 | 52 | 63.2 | THF | 10 | −5–40 | 0.49 | 42 |
| 10 | " | 1248. | 48.2 | 1039.8 | 1263.1 | THF | 500 | −5–15 | 9.8 | 41 |
| 11 | " | 45.6 | 1.6 | 52 | 63.2 | THF | 20 | −5–40 | 0.49 | 36 |
| 12 | " | 45.6 | 1.0 | 52 | 63.2 | THF | 20 | 0–50 | 0.49 | 35 |
| 13 | " | 45.6 | 0.4 | 52 | 63.2 | THF | 20 | 0–52 | 0.49 | 34 |
| 14 | " | 50 | 1.0 | 52 | 63.2 | THF | 30 | −5–30 | 0.49 | 39 |
| 15 | " | 50 | 1.0 | 52 | 63.2 | DGM | 10 | −5–15 | 0.49 | 30 |
| 16 | " | 50 | .6 | 52 | 63.2 | THF | 30 | −5–39 | 0.49 | 40 |
| 17 | " | 50 | .4 | 52 | 63.2 | THF | 30 | −5–54 | 0.49 | 37 |
| 18 | " | 1000 | 20.1 | 1039.8 | 1263.1 | THF | 400 | −5–12 | 9.76 | 36 |
| 19 | " | 1000 | 20.1 | 1039.8 | 1263.1 | THF | 300 | −5–15 | 9.76 | 42* |
| 20 | " | 1000 | 20.1 | 1039.8 | 1263.1 | THF | 300 | −5–15 | 9.76 | 43* |
| 21 | " | 1200 | 20.1 | 1039.8 | 1263.1 | THF |  | −5–15 | 9.76 | 39 |
| 22 | " | 5120 | 161.0 | 5200 | 6315.5 | THF | 2000 | −5–15 | 48.8 | 43* |

[a]Exchange "Catalyst", Titanocene dichloride (dicyclopentadiene titanium dichloride)
Exchange Reaction Temp. 25° C.
[b]THF = Tetrahydrofuran
DGM - Diethylene glycol dimethyl ether (diglyme)
[c]Yield by GLC unless otherwise noted by an * for distilled yield

TABLE IV

Preparation of 7(Z),11(Z,E)-Hexadecadien-1-ol using Various Solvents at Room Temperature for Grignard Exchange Reaction and No Catalyst for the Ethylene Oxide Addition

| Run | R | RMgCl mmoles | Cp$_2$TiCl$_2$[a] mmoles | 1,5,9-Tetra-decatriene mmoles | Ethylene Oxide (EO) Reaction mmoles | Solvent type[b] | mL | temp. °C. | Yield % GLC |
|---|---|---|---|---|---|---|---|---|---|
| 23 | i-Pr | 62.4 | 2.6 | 52 | 101 | THF | 50 | 0–25 | 11 |
| 24 | i-Pr | 62.4 | 2.6 | 52 | 101 | THF | 100 | 0–25 | 6 |
| 25 | i-Pr | 62.4 | 2.6 | 52 | 101 | THF | 50 | 5–Reflux | 9 |
| 26 | i-Pr | 62.4 | 2.6 | 52 | 101 | Et$_2$O / Et$_2$O | 100 / 50 | " | 9 |
| 27 | i-Bu | 62.4 | 2.6 | 52 | 101 | THF | 50 | " | 6 |
| 28 | i-Bu | 62.4 | 2.6 | 52 | 101 | Et$_2$O | 50 | " | 16 |
| 29 | i-Bu | 62.4 | 2.6 | 52 | 50.5 | THF | 50 | " | 4 |
| 30 | i-Bu | 62.4 | 2.6 | 52 | 50.5 | Et$_2$O | 50 | " | 18 |
| 31 | i-Bu | 62.4 | 2.6 | 52 | 151.5 | Et$_2$O | 50 | " | 29 |
| 32 | i-Bu | 62.4 | 2.6 | 52 | 101 | Et$_2$O / Toluene | 50 / 100 | " | 14 |
| 33 | i-Bu | 62.4 | 2.6 | 52 | 151.5 | n-Bu$_2$O | 50 | " | 25 |
| 34 | n-Bu | 62.4 | 2.6 | 52 | 151.5 | Et$_2$O | 50 | −20–Reflux | 48 |
| 35 | n-Bu | 78.0 | 2.6 | 52 | 151.5 | Et$_2$O | 50 | 0 to Reflux | 43 |
| 36 | n-Bu | 78.0 | 2.6 | 52 | 151.5 | n-Bu$_2$O | 50 | −5 to Reflux | 37 |
| 37 | n-Bu | 120.0 | 2.6 | 52 | 151.5 | Et$_2$O | 50 | −5 to Reflux | 26 |
| 38 | n-Bu | 64.0 | 1.3 | 52 | 151.5 | n-Bu$_2$O | 50 | −20 to Reflux | 34 |

[a]Titanocene dichloride (dicyclopentadiene titanium dichloride)
[b]THF = Tetrahydrofuran
Et$_2$O = diethyl ether
n-Bu$_2$O = di-n-butyl ether

TABLE V

Preparation of 7(Z),11(Z,E)-Hexadecadien-1-ol from 1,5(Z),9(Z,E)-Tetradecatriene using Grignard Exchange Reaction at Room Temperature Followed by Addition of Ethylene Oxide

| Run | Grignard Reagent RMgCl R | mmoles | Exchange Catalyst Cp$_2$TiCl$_2$[a] mmoles | 1,5,9-Tetradecatriene mmoles | Ethylene Oxide (EO) Reaction (EO) mmoles | Solvent type[c] | mL | temp. °C. | CuBr Catalyst mmoles | Yield % (GLC) |
|---|---|---|---|---|---|---|---|---|---|---|
| 39 | n-Bu | 64 | 1.6 | 52 | 101 | — | — | −20–Reflux | 0 | 34 |
| 40 | n-Bu | 62 | TiCl$_4$ 2.7[b] | 52 | 101 | Et$_2$O | 50 | −20–Reflux | 0 | 44 |
| 41 | n-Bu | 4974 | 208. | 5199. | 10,400 | Et$_2$O | 1100 | −40–70 | 0 | 34 |
| 42 | n-Bu | 62.4 | 2.6 | 52 | 63.2 | Et$_2$O | 50 | −30–0 | 7.8 | 31 |
| 43 | n-Bu | 62.4 | 2.6 | 52 | 63.2 | THF | 50 | −30–44 | 7.8 | 40 |
| 44 | n-Bu | 62.4 | 2.6 | 54 | 63.2 | THF | 50 | −30–3 | 7.8 | 44 |
| 45 | n-Bu | 62.4 | 2.6 | 52 | 63.2 | THF | 50 | −30–16 | 7.8 | 35 |
| 46 | n-Bu | 62.4 | 2.6 | 52 | 63.2 | THF | 50 | 0–42 | 7.8 | 32 |
| 47 | n-Bu | 62.4 | 2.6 | 52 | 63.2 | THF | 75 | 0–3 | 7.8 | 33 |
| 48 | n-Bu | 62.4 | 2.6 | 52 | 63.2 | THF | 75 | 10–25 | 7.8 | 26 |
| 49 | n-Bu | 62.4 | 2.6 | 52 | 63.2 | THF | 25 | 0–7 | 7.8 | 35 |
| 50 | n-Bu | 62.4 | 2.6 | 52 | 98.7 | THF | 25 | 0–6 | 7.8 | 28 |
| 51 | n-Bu | 62.4 | 2.6 | 52 | 63.2 | THF |  | 0 | 7.8 | 36 |
| 52 | n-Bu | 62.4 | 2.6 | 52 | 63.2 | THF | 25 | <5 | 3.9 | 36 |
| 53 | n-Bu | 62.4 | 2.6 | 52 | 53.3 | THF | 25 | 0 | 7.8 | 30 |
| 54 | n-Bu | 62.4 | 2.6 | 52 | 53.3 | THF | 25 | 0 | 3.9 | 33 |
| 55 | n-Bu | 62.4 | 2.6 | 52 | 63.2 | THF | 25 | −10–37 | 7.8 | 27 |
| 56 | n-Bu | 62.4 | 2.6 | 52 | 63.2 | THF | 25 | −10–27 | 11.7 | 26 |

[a]Cp$_2$TiCl$_2$ = Titanocene dichloride (dicyclopentadienyl titanium dichloride)
[b]Exchange reaction temperature = reflux for 22 hours; others at room temperature approximately 2 hours.
[c]Et$_2$O = diethyl ether
THF = Tetrahydrofuran The data in Table III indicate that the results are fairly consistent over more than an 80-fold increas in the scale of the reaction. Runs 1–6 show that only very small amounts of copper (I) bromide are required to produce good results in the reaction of ethylene oxide with the Grignard intermediate under the conditions used. Table IV shows that presence of CuBr is necessary when the solvent is THF but may not be necessary in ether.

Run 40, Table V, shows that TiCl$_4$ can be used effectively in ether solutions in place of titanocene dichloride in the transfer of MgCl from the butyl Grignard to the tetradecatriene moiety.

EXAMPLE VII

Coupling of 1,5,9-Tetradecatriene with Bromethyl Acetate using Butylmagnesium Chloride 1,5,9-Tetradecatriene (10 g, 0.052 mol), n-butylmagnesium chloride (24.8 mL of 2.5M in tetrahydrofuran; 0.062 mol) and titanium tetrachloride (0.52 g, 0.0027 mol) were stirred under an inert atmosphere at about 65° C. for about 4.5 hours. The reaction mixture was then cooled to 0° C. and cuprous bromide (0.14 g, 1.0 mmol) was added. 2-Bromoethyl acetate (6.9 mL, 0.063 mol) was then added dropwise and the mixture allowed to warm slowly to room temperature and stirred for several hours at room temperature. Reaction temperature was then raised to 60° C. for 4 hours before the mixture was cooled, acidified with aqueous HCl, then extracted with hexane. The hexane extract was washed with saturated sodium bicarbonate solution, dried over MgSO$_4$, filtered and solvent removed on the rotary evaporator. GLC analysis of this crude reaction product indicated an 11% yield of gossyplure. It should be recognized that while this reaction represents successful production of gossyplure from 1,5,9-tetradecatriene in one reaction vessel, the reaction parameters have not been optimized. Consequently, significantly improved yields of gossyplure can be expected upon optimization of various reaction parameters.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

That which is claimed:

1. A process for the synthesis of gossyplure (7(Z), 11(Z,E)-hexadecadienyl acetate) which comprises:
   (a) disproportionating 1,5-cyclooctadiene and 1-hexane in the presence of a disproportionation catalyst under disproportionation conditions suitable to produce 1,5,9-tetradecatriene;
   (b) metallating the 1,5,9-tetradecatriene obtained in step (a) with a metallating agent under suitable conditions to form a 1-metallo-5,9-tetradecadiene, having the empirical formula C$_{14}$H$_{25}$M wherein M is selected from the group consisting of MgX, MgR', BR$_2$, AlR$_2$, and (Ar)$_2$ZrX wherein X is Cl, Br or I, each R is independently a C$_1$ to C$_{10}$ carbon radical wherein at least one R group is selected from the group consisting of secondary and tertiary alkyl groups, and each R can be connected to the other as part of a ring structure; R' is a C$_2$ to C$_{10}$ carbon radical and Ar is an aromatic ligand having 5–10 carbon atoms;
   (c) contacting the 1-metallo-5,9-tetradecatriene with a C$_2$-synthon which is reactive with the terminally substituted organometallic bond under conditions suitable to form a 1-substituted-7,11-hexadecadiene, having the empirical formula C$_{15}$H$_{27}$Z; wherein Z is selected from the group consisting of

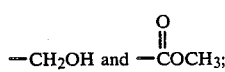

and (d) converting Z into the acetate moiety, —CH$_2$OCOCH$_3$.

2. A process in accordance with claim 1 wherein said disproportionation catalyst is (phenylmethoxycarbene)-pentacarboxyltungsten(O).

3. A process in accordance with claim 2 wherein step (a) is carried out at a temperature in the range of 40°–100° C., pressure in the range of 50–1200 psig, for a period of time in the range of 0.5–18 hours.

4. A process in accordance with claim 1 wherein said metallating agent is a compound selected from the group consisting of:

R$_2$AlH,

R$_2$BH,

R'MgX,

R$_2$'Mg, and (Ar)$_2$Zr(X)H wherein each R is independently a C$_1$ to C$_{10}$ carbon radical wherein at least one R group is selected from the group consisting of secondary and tertiary alkyl groups, and each R group can be connected to the other as part of a ring structure; wherein R' is a C$_1$ to C$_{10}$ carbon radical; wherein Ar is an aromatic ligand having 5–10 carbon atoms; and wherein X is Cl, Br or I.

5. A process in accordance with claim 1 wherein said metallating agent is

R$_2$BH wherein R is as defined above.

6. A process in accordance with claim 5 wherein R$_2$BH is 9-borabicyclononane.

7. A process in accordance with claim 1 wherein said metallating agent is

R'MgX wherein R' and X are as defined above.

8. A process in accordance with claim 1 wherein said C$_2$-synthon is a compound selected from the group consisting of:
ethylene oxide,
ethyl bromoacetate, and
bromoethyl acetate.

9. A process in accordance with claim 5 wherein said C$_2$-synthon is ethyl bromoacetate.

10. A process in accordance with claim 9 wherein step (d) comprises:
(i) reducing Z from

to —CH$_2$OH with lithium aluminum hydride; and
(ii) esterifying the —CH$_2$OH unit to form —CH$_2$OCOCH$_3$.

11. A process in accordance with claim 7 wherein said C$_2$-synthon is ethylene oxide.

12. A process in accordance with claim 11 wherein step (d) comprises:

(i) esterifying the —CH$_2$OH unit to form —CH$_2$OCOCH$_3$.

13. A process for the synthesis of gossyplure (7(Z), 11(Z,E)-hexadecadienyl acetate) which comprises:
(a) disproportionating 1,5-cyclooctadiene and 1-hexene in the presence of a disproportionation catalyst under disproportionation conditions suitable to produce 1,5,9-tetradecatriene;
(b) metallating the 1,5,9-tetradecatriene obtained in step (a) with a metallating agent under suitable conditions to form a 1-metallo-5,9-tetradecadiene, having the empirical formula C$_{14}$H$_{25}$M wherein M is selected from the group consisting of MgX, MgR', BR$_2$, AlR$_2$, and (Ar)$_2$ZrX wherein X is Cl, Br or I, each R is independently a C$_1$ to C$_{10}$ carbon radical wherein at least one R group is selected from the group consisting of secondary and tertiary alkyl groups, and each R can be connected to the other as part of a ring structure; R' is a C$_2$ to C$_{10}$ carbon radical and Ar is an aromatic ligand havig 5–10 carbon atoms;
(c) contacting the 1-metallo-5,9-tetradecatriene with bromoethyl acetate under conditions suitable to form gossyplure.

14. A process in accordance with claim 13 wherein said disproportionation catalyst is (phenylmethoxycarbene)pentacarboxyltungsten(O).

15. A process in accordance with claim 14 wherein step (a) is carried out at a temperature in the range of 40°–100° C., pressure in the range of 50–1200 psig, for a period of time in the range of 0.5–18 hours.

16. A process in accordance with claim 13 wherein said metallating agent is a compound selected from the group consisting of:

R$_2$AlH

R$_2$BH,

R'MgX,

R$_2$'Mg, and (Ar)$_2$Zr(X)H wherein each R is independently a C$_1$ to C$_{10}$ carbon radical wheren at least one R group is selected from the group consisting of secondary and tertiary alkyl groups, and each R group can be connected to the other as part of a ring structure; wherein R' is a C$_1$ to C$_{10}$ carbon radical; wherein Ar is an aromatic ligand having 5–10 carbon atoms; and wherein X is Cl, Br or I.

17. A process in accordance with claim 13 wherein said metallating agent is

R$_2$BH wherein R is as defined above.

18. A process in accordance with claim 17 wherein R$_2$BH is 9-borabicyclononane.

19. A process in accordance with claim 13 wherein said metallating agent is

R'MgX wherein R' and X are as defined above.

* * * * *